United States Patent [19]

Tenerz et al.

[11] Patent Number: 5,018,529
[45] Date of Patent: May 28, 1991

[54] MINIATURIZED SENSOR FOR PHYSIOLOGICAL PRESSURE MEASUREMENTS

[75] Inventors: Lars Tenerz, Uppsala; Bertil Höök, Västeras, both of Sweden

[73] Assignee: Radisensor AB, Uppsala, Sweden

[21] Appl. No.: 473,054

[22] Filed: Jan. 31, 1990

Related U.S. Application Data

[63] Continuation of Ser. No. 285,966, filed as PCT SE87/00294 on Jun. 24, 1987, published as WO88/00023 on Jan. 14, 1988, abandoned.

[30] Foreign Application Priority Data

Jun. 25, 1986 [SE] Sweden ............................ 8602836

[51] Int. Cl.$^5$ ............................................. A61B 5/02
[52] U.S. Cl. ................................. 128/667; 128/675; 128/748; 73/705
[58] Field of Search ....................... 128/672–675, 128/664–667, 633–634, 748; 73/705, 708, 715

[56] References Cited

U.S. PATENT DOCUMENTS

| | | |
|---|---|---|
| 3,789,667 | 2/1974 | Porter et al. |
| 4,274,423 | 6/1981 | Mizuno et al. ...................... 128/675 |
| 4,456,013 | 6/1984 | DeRossi et al. ................ 128/748 X |
| 4,487,206 | 12/1984 | Aagard ................................. 128/667 |
| 4,543,961 | 10/1985 | Brown ........................... 128/675 X |
| 4,593,701 | 6/1986 | Kobayashi et al. ............ 128/673 X |
| 4,611,600 | 9/1986 | Cohen ................................... 128/667 |
| 4,691,708 | 9/1987 | Kane .............................. 128/675 X |

FOREIGN PATENT DOCUMENTS

59-154333 9/1984 Japan .
441725 11/1985 Sweden .

OTHER PUBLICATIONS

IEEE Transactions on Bio-Medical Engineering, vol. BME-17, No. 3, pp. 207–219, Jul. 3, 1970, "Miniaturized Pressure Transducer Intended for Intravascular Use"—Lars H. Lindstrom.
Digest of the 11th International Conference on Medical and Biological Engineering—1976—Ottawa, "Development and Evaluatoin of Fiber Optic Pressure Catheter" by Saito and Masumoto, pp. 690–691.
30th AEMB—Los Angeles, Nov. 5–9, 1977, "An Improved Fiberoptic Catheter for Intravascular Pressure and Sound Measurements", p. 292 by French and Gerhard.

Primary Examiner—Ruth S. Smith
Attorney, Agent, or Firm—Foley & Lardner

[57] ABSTRACT

Miniaturized sensor for physiological pressure measurements in situ, including an elastic sleeve (1) with a diaphragm portion through which the hydrostatic pressure is transmitted as a force acting on a light conductor (2) which is supplied with light from an external source and fixed to a support body (3) such that the hydrostatic pressure variations cause elastic, relative positional variations between the end surface (4) of the light conductor (2) and a light-reflecting surface (5) on the support body (3), which in turn gives rise to variations in reflected light intensity transmitted back through the light conductor (2), to serve as a pressure signal.

13 Claims, 2 Drawing Sheets

MINIATURIZED SENSOR FOR PHYSIOLOGICAL PRESSURE MEASUREMENTS

This application is a continuation, of application Ser. No. 07/285,966, filed Dec. 14, 1988, now abandoned.

BACKGROUND OF THE INVENTION

Pressure measurements in human organs are an important source of information for diagnosing different states of illness. In the heart and blood vessel system, pressure measurements give information as to the pumping capacity of the heart, the closing and opening functions of the ventricles, constrictions and deposits in blood vessels, as well as deviations from the normal state in the peripheral network of blood vessels. Pressure measurements can also give valuable diagnostic information when applied to the different parts of the digestive system, from the throat to the anus. The state of urethras, spine as well as uterus is also diagnosed by pressure measurements, as well as several of the liquid filled body cavities such as the intracranial cavity, the spinal cord and the uterus.

Often both static pressure and dynamic pressure sequences are measured.

Conventional measurement techniques are based on hydraulic pressure transmission in liquid filled catheters between the measurement site and an externally placed pressure indicator. Such a system seldom manages to record pressure vibrations of a higher frequency than some tens of Hertz. The limitation is caused by the inertia of the liquid in combination with elastic components, which give rise to resonance phenomena. The properties are seldom completely stable but are drastically affected by such as the presence of microscopic air bubbles.

The problems discussed above can be solved by miniaturized pressure sensors which are applied directly to the measurement site, the measuring signal being transmitted via electrical or optical fibers. A number of examples of such arrangements have been published and these have also resulted in commercially available products (IEEE TRANSACTIONS ON BIO-MEDICAL ENGINEERING. Vol. BME-17, No. 3. p. 207-209, July 3, 1970, "MINIATURIZED PRESSURE TRANSDUCER INTENDED FOR INTRAVASCULAR USE" by Lars Lindstrom and DIGEST OF THE 11th INTERNATIONAL CONFERENCE ON MEDICAL AND BIOLOGICAL ENGINEERING- 1976 OTTAWA, "DEVELOPMENT AND EVALUATION OF FIBER OPTIC PRESSURE CATHETER" by Saito and Masumoto, p. 690, and "30 th ACMB" LOS ANGELES, Nov. 5-9, 1977, "AN IMPROVED FIBEROPTIC CATHETER FOR INTRAVASCULAR PRESSURE AND SOUND MEASUREMENTS" p. 292 by French and Gerhard). Their clinical use has been extremely limited, however. The reason for this is primarily that the degree of miniaturization has not been sufficient. The commercially available sensors have an outer diameter of from 1.5 mm and upwards. This implies that clinical routines must be departed from, and in some cases a surgical operation will be necessary. Often, such complications can not be accepted, which has meant that the use of the miniaturized sensors has been very limited. Another important factor is the high price of the sensors, which is partly a consequence o their relatively complex fabrication, with a plurality of complicated elements, the assembly of which has often taken place using manual methods. The absence of functioning calibration routines is a further factor which has limited the spread of the miniaturized sensors.

The present invention provides a solution to these and associated problems, since it relates to the fabrication of a miniaturized pressure sensor which can have an exterior diameter of 0.5 mm. This allows the sensor to be used without needing to depart from established clinical routines. The sensor can be inserted through ordinary injection needles and catheters, even into narrow blood vessels and cavities. The sensor is manufactured with materials and methods adapted from semiconductor technology, which results in a low cost. Manual and manipulative fabrication steps are replaced with the batch production of hundreds of elements at the same time. Furthermore, the small dimensions afford a practical solution to the calibration problems apparent from the Swedish patent 441 725.

The distinguishing features for the pressure sensor in accordance with the invention are disclosed in the accompanying claims.

BRIEF DESCRIPTION OF THE DRAWINGS

A preferred embodiment of the invention will now be described in the following, and in connection with the accompanying drawings, on which

DESCRIPTION OF THE PREFERRED EMBODIMENT

Figure 1:
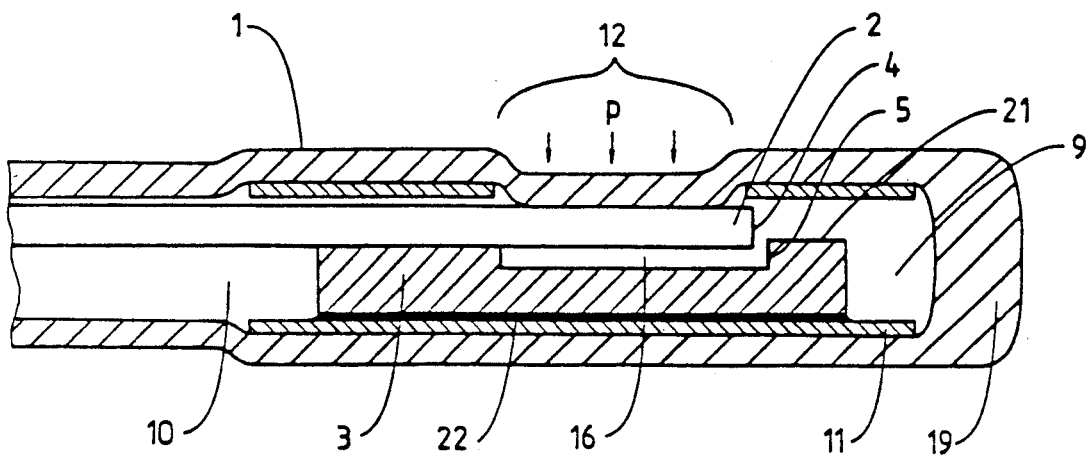
FIG. 1 is a basic embodiment of the pressure sensor in accordance with the invention.

The functional principle of the sensor is illustrated in FIG. 1. Light from an externally placed instrument unit is passed via a light conductor, optical fiber 2 to the sensor structure itself. The light conductor 2 may be a glass or plastics fiber, with core and cladding of different optical refractive indices in accordance with the state of the art. In the sensor structure, the light conductor 2 is rigidly mounted on a body 3, which has a form enabling the end surface 4 of the light conductor 2 to be placed adjacent a specularly reflecting surface 5 on the body 3. Between the end portion of the light conductor 2 and the body there is a space 16 enabling elastic bending movements of the end portion. Such bending movements are induced by hydrostatic pressure applied to the diaphragm portion of an elastic sleeve 1, this portion being in contact with the flexing end portion of the conductor. The elastic sleeve, made from such as silicone or similar material, is stretched over a catheter tube 11 surrounding the body 3 and the flexing end portion of the conductor 2, thus forming a tight sheath surrounding the sensor. In the wall of the tube 11 there is an aperture 12 enabling the transfer of force from the diaphragm portion of the sleeve 1 to the flexing end portion of the light conductor 2. The sleeve 1 thus has the form of a surrounding jacket which is closed off at one end, whereby the inner cavity 9 of the sensor is separated from its nearest surroundings. The cavity 9 does have, however, communication with the surrounding air pressure via a venting duct 10. This duct extends parallel to the light conductor 2, which is also used for signal transmission to an instrument unit connected to it. Light from the end surface 4 of the light conductor 2 is reflected at the surface 5 on the body 3, and the reflected light intensity is dependent on the mutual relationship between the end surface 4 and surface 5.

Figure 2:
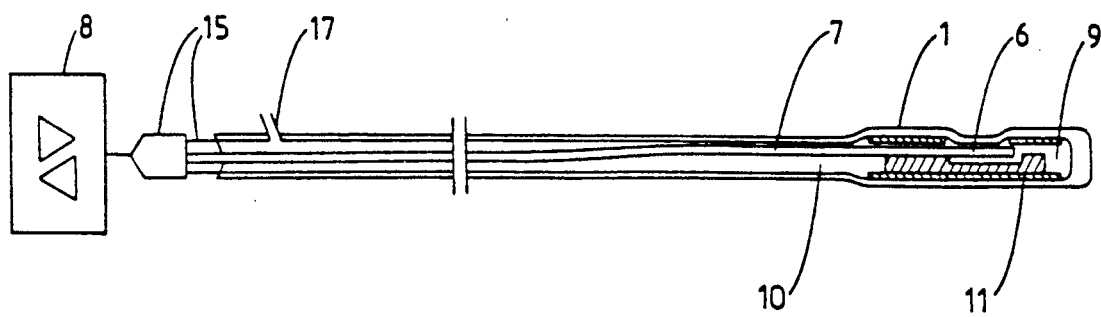
FIG. 2 illustrates the sensor in a complete measuring system.

FIG. 2 illustrates how the sensor is connected to an exterior instrument unit 8. This connection suitably takes place with the aid of fiber-optical connector 15. The instrument unit 8 includes a light source, e.g. a light emitting diode, a detector, e.g. a photo diode, and a fiber optic branch. In addition, the unit contains an amplifier, control unit and display unit e.g. a printer or chart recording instrument.

The embodiment of the sensor illustrated in FIG. 2 is one where the light conductor is in two parts 6 and 7, in order to facilitate manufacture. There is also a vent hole 17 to ensure that the venting duct 10 is in communication with ambient air pressure.

Figure 3:
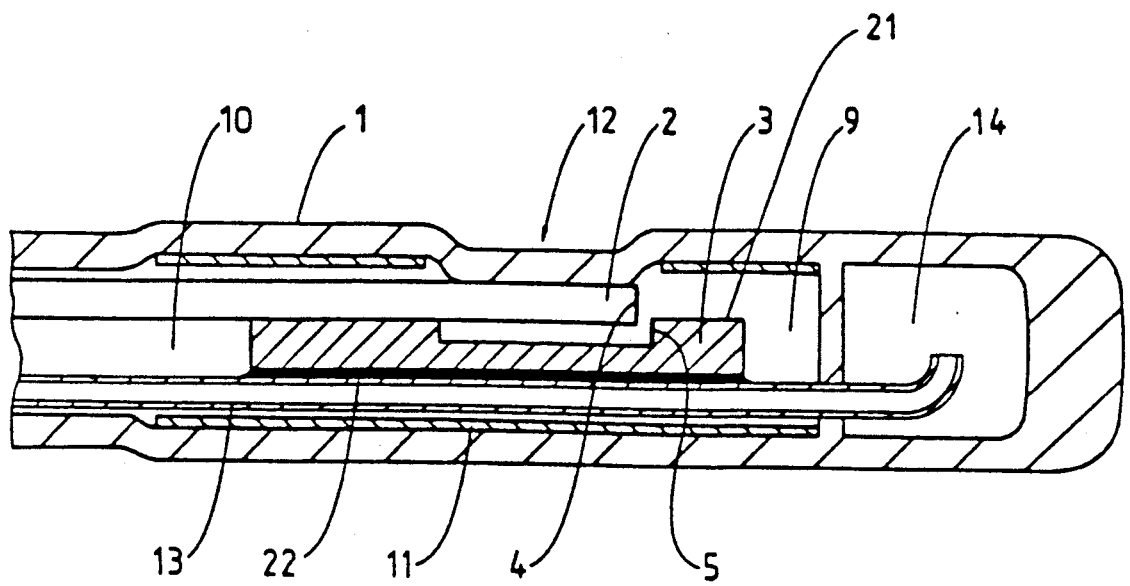
FIG. 3 is an embodiment of the sensor with a special calibration function.

FIG. 3 illustrates an embodiment permitting simplified calibration of the sensor. The sensor structure, with the lightwave conductor 2, sleeve 1 and body 3 is extended in the probing direction to include a cavity 14 with elastic walls, suitably manufactured from the same material as, and integral with the sleeve 1. Via a duct 13 the cavity 14 is in communication with an externally placeable pump means, e.g. a hypodermic syringe. The cavity 14 can thus be inflated to expand and seal against the inner wall of a surrounding catheter. The pressure sensor will thus be accessible for the calibrating pressure applied through this catheter (c.f. Swedish patent 441 725).

Figures 4A, 4B:
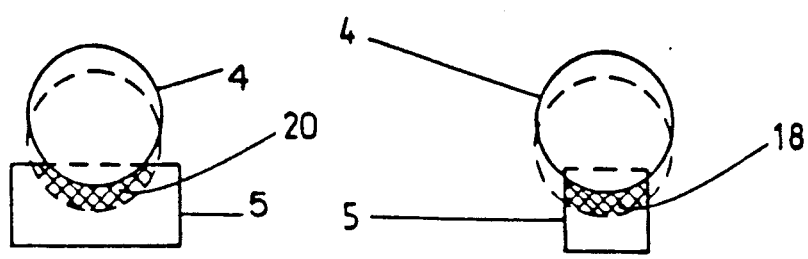
FIGS. 4a and 4b are schematic axial views of parts of the sensor.

FIGS. 4a and 4b are schematic axial views of the light conductor end 4 and the reflecting surface 5. In FIG. 4a the width of the body 3 is greater than the diameter of the light conductor 2, while the opposite is the case in FIG. 4b. The hatched areas 18 and 20 represent the increment in reflected light intensity obtained for a given relative positional change between the surfaces 4 and 5. Due to the circular cross section of the light conductor, there is non-linearity in the case depicted in 4a, while the case depicted in 4b gives a substantially linear relationship, and is thus the most favorable of the two in this respect. Several detailed implementations are possible to achieve the same effect, e.g. the side edges, vertical in the figures, of the reflecting surface 5 can be chamfered.

The shape of the body 3 can be obtained in several ways. A suitable method is to utilize single-crystal silicon as material. The reflecting surface 5 can then constitute an elementary crystal plane, e.g. the (111)-plane or the (100)-plane, according to Miller's nomenclature for cubic crystal symmetry. In several etching liquids, e.g. potassium hydroxide, the etching rate is lower in both these crystal plane directions compared with those of higher orders. In so-called pattern etching, i.e. etching with a lithographic mask of given pattern, the elementary planes will be formed after the etching liquid has acted for a longer time. The anisotropy of the etching also causes the resulting surface to have great smoothness and thus good specular reflection. By thin film coating, e.g. with aluminium, the reflectivity can be further improved.

In pattern etching the initial material is suitably a large wafer of single-crystal silicon, from which a larger number of units can be manufactured simultaneously. This enables good manufacturing economy, in spite of the extreme demands on dimensional tolerances and surface finish. Usually, a silicon wafer of a diameter of 5–150 mm and a thickness of 0.2–0.4 mm is used. The crystalline orientation of the wafer is usually such that the flat surfaces are (100)-planes or (110)-planes. These surfaces are allowed to form the three main surfaces 21, 22 of the body. For the etching, the reflecting surface 5 may be a (100)-plane in the former case and in the latter case a (111)-plane. Etching is carried out so that a mask defines the longitudinal extension of the space 16, while the etching time determines the depth of the space. The mask can further define the width of the reflecting surface 5, as well as the width of the entire body 3. The situation is namely that the individual bodies 3 can be broken off from the original wafer if stress concentrations in the form of longitudinal grooves are simultaneously etched together with the space 16. Alternatively, the wafer can be parted into the individual bodies 3 by sawing with a diamond saw.

One skilled in the art will understand that the invention can be varied in many ways within the scope of the accompanying claims.

We claim:

1. A miniaturized pressure sensor for physiological pressure measurements in situ, comprising:
   a sleeve of elastic material having a proximate end and a distal end;
   a diaphragm formed at the distal end of said sleeve;
   a light conductor extending through said sleeve and having a corresponding proximal end and a corresponding distal end for transmitting light from said corresponding proximal end to said corresponding distal end, said corresponding distal end having an end surface;
   a light reflecting surface located opposite said corresponding distal end of the light conductor in a fixed position relative to the sleeve for receiving light from said corresponding distal end of the light conductor and to reflect a portion thereof back into the light conductor;
   a portion of said corresponding distal end of said light conductor being in contact with the diaphragm to deflect the end surface of the light conductor in response to pressure forces acting on the diaphragm so as to modulate the intensity of the reflected light; and
   support means arranged in the distal end of said sleeve to support said corresponding distal end of said light conductor in a cantilever fashion, said light reflecting surface being formed on a surface of said support means.

2. A miniaturized pressure sensor as claimed in claim 1, wherein said support means is a single-crystal silicon body having defining surfaces and wherein said light reflecting surface comprises an elementary crystal plane.

3. A miniaturized pressure sensor as claimed in claim 2, wherein all of said defining surfaces form right angles.

4. A miniaturized pressure sensor as claimed in claim 3, wherein the end surface of the light conductor is circular and the light reflecting surface has a width measured in a direction at right angles to the direction in which the end surface moves in response to the pressure variations, which is less than the diameter of the end surface.

5. A miniaturized pressure sensor as claimed in claim 4, wherein said light reflecting surface comprises a thin film of highly reflective material such as aluminum.

6. A miniaturized pressure sensor as claimed in claim 5, wherein said light reflecting surface is a (100)-plane of said single-crystal silicon body.

7. A miniaturized pressure sensor as claimed in claim 6, wherein said body includes main surfaces and wherein said main surfaces of said body both are (100)-planes.

8. A miniaturized pressure sensor as claimed in claim 5, wherein said body includes main surfaces, and wherein said light reflecting surface is a (111)-plane and the main surfaces of the body are (110)-planes.

9. A miniaturized pressure sensor as claimed in claim 4, wherein said sleeve defines an inner, air-filled cavity which via an air-filled duct is in communication with a reference pressure, and wherein at least one tube extends parallel to the light conductor, said at least one tube extending through a wall of elastic material provided in said sleeve forwardly of said support means and opening into a chamber formed by said wall and an interior portion of a distal portion of said distal end of said sleeve.

10. A miniaturized pressure sensor as claimed in claim 1, wherein said support means has a recess defined therein opposite said corresponding distal end of said light conductor.

11. A miniaturized pressure sensor as claimed in claim 10, wherein said light reflecting surface is integral with a wall of said recess.

12. A miniaturized pressure sensor as claimed in claim 1, further comprising a protective tube disposed within said sleeve and surrounding said support means, said tube having an opening defined therein, said opening being located adjacent said diaphragm.

13. A miniaturized pressure sensor as claimed in claim 1, wherein said diaphragm is formed integrally with said sleeve.

* * * * *